United States Patent
Pasquereau et al.

(10) Patent No.: US 6,513,397 B2
(45) Date of Patent: Feb. 4, 2003

(54) PROCESS AND UNIT FOR SAMPLING ALDEHYDES AND KETONES CONTAINED IN EXHAUST GASES

(75) Inventors: Michel Pasquereau, Sartrouville (FR); Jean-François Papagni, Saint Rémy les Chevreuses (FR); Richard Levesque, Suresnes (FR); Laurent Dayde, Suresnes (FR)

(73) Assignee: Institut Francais du Petrole, Rueil Malmaison-Cedex (FR)

( * ) Notice: Subject to any disclaimer, the term of this patent is extended or adjusted under 35 U.S.C. 154(b) by 15 days.

(21) Appl. No.: 10/011,737

(22) Filed: Dec. 11, 2001

(65) Prior Publication Data

US 2002/0043116 A1 Apr. 18, 2002

Related U.S. Application Data

(62) Division of application No. 09/344,807, filed on Jun. 25, 1999, now Pat. No. 6,339,965.

(30) Foreign Application Priority Data

Jun. 25, 1998 (FR) ............................................. 98 08113

(51) Int. Cl.⁷ ................................................. G01N 1/22
(52) U.S. Cl. ................................ 73/863.33; 73/863.23; 73/863.31
(58) Field of Search ...................... 73/863.01, 863.02, 73/863.03, 863.12, 863.21, 863.57, 863.61, 863.71, 864.73, 23.31, 863.31, 863.23

(56) References Cited

U.S. PATENT DOCUMENTS

| 3,406,562 A | | 10/1968 | Perna, Jr. et al. ............ 73/23.31 |
|---|---|---|---|
| 3,547,587 A | * | 12/1970 | Innes ........................... 436/134 |
| 4,596,156 A | * | 6/1986 | Shimizu et al. ........... 73/863.31 |
| 4,704,910 A | | 11/1987 | Conrad ................. 73/863.31 X |
| 4,758,521 A | | 7/1988 | Lushbaugh .................. 430/128 |
| 4,759,210 A | | 7/1988 | Wohltjen .................. 73/23.2 X |
| 4,779,466 A | | 10/1988 | Romsner et al. .......... 73/863.33 |
| 5,205,988 A | | 4/1993 | Tanaka et al. ................. 422/93 |
| 5,233,876 A | * | 8/1993 | LaPack et al. ............ 73/863.33 |
| 5,279,146 A | * | 1/1994 | Asano et al. ............... 73/28.04 |
| H1305 H | | 5/1994 | Townsend et al. ............. 44/449 |
| 5,599,357 A | | 2/1997 | Leeper .......................... 44/355 |
| 5,709,082 A | | 1/1998 | Harris et al. ........... 73/23.31 X |
| 6,134,942 A | * | 10/2000 | Pasquereau et al. ........ 73/23.31 |

FOREIGN PATENT DOCUMENTS

| DE | 3822360 | 1/1990 | ................... 422/88 |
|---|---|---|---|
| DE | 4217263 | 12/1993 | |
| EP | 047434 | 3/1982 | ................... 204/425 |
| EP | 272552 | 6/1988 | ................... 436/128 |
| EP | 316688 | 5/1989 | |
| EP | 429143 | 5/1991 | ................... 73/23.2 |
| JP | 63-132161 | 6/1988 | |
| JP | 3-232516 | 10/1991 | ................... 423/245 |
| JP | 3-242534 | 10/1991 | ................... 73/23.31 |
| JP | 6-34500 | 2/1994 | ................... 73/864.73 |
| JP | 6-265475 | 9/1994 | ................... 73/23.31 |

* cited by examiner

*Primary Examiner*—Thomas P. Noland
(74) *Attorney, Agent, or Firm*—Antonelli, Terry, Stout & Kraus, LLP

(57) ABSTRACT

A unit for sampling aldehydes and ketones contained in diluted exhaust gases from thermal combustion engines has a specific trapping circuit and a simulation circuit that simulates the specific trapping circuit. The specific trapping circuit and the simulation circuit are arranged in parallel so that the diluted gases can be passed for some time in the simulation circuit (5) before they are passed into the specific trapping circuit wherein aldehydes and ketones are trapped.

9 Claims, 1 Drawing Sheet

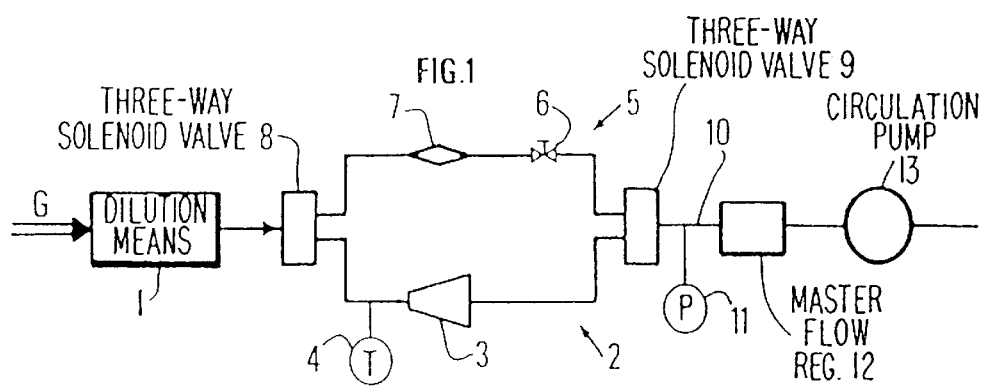
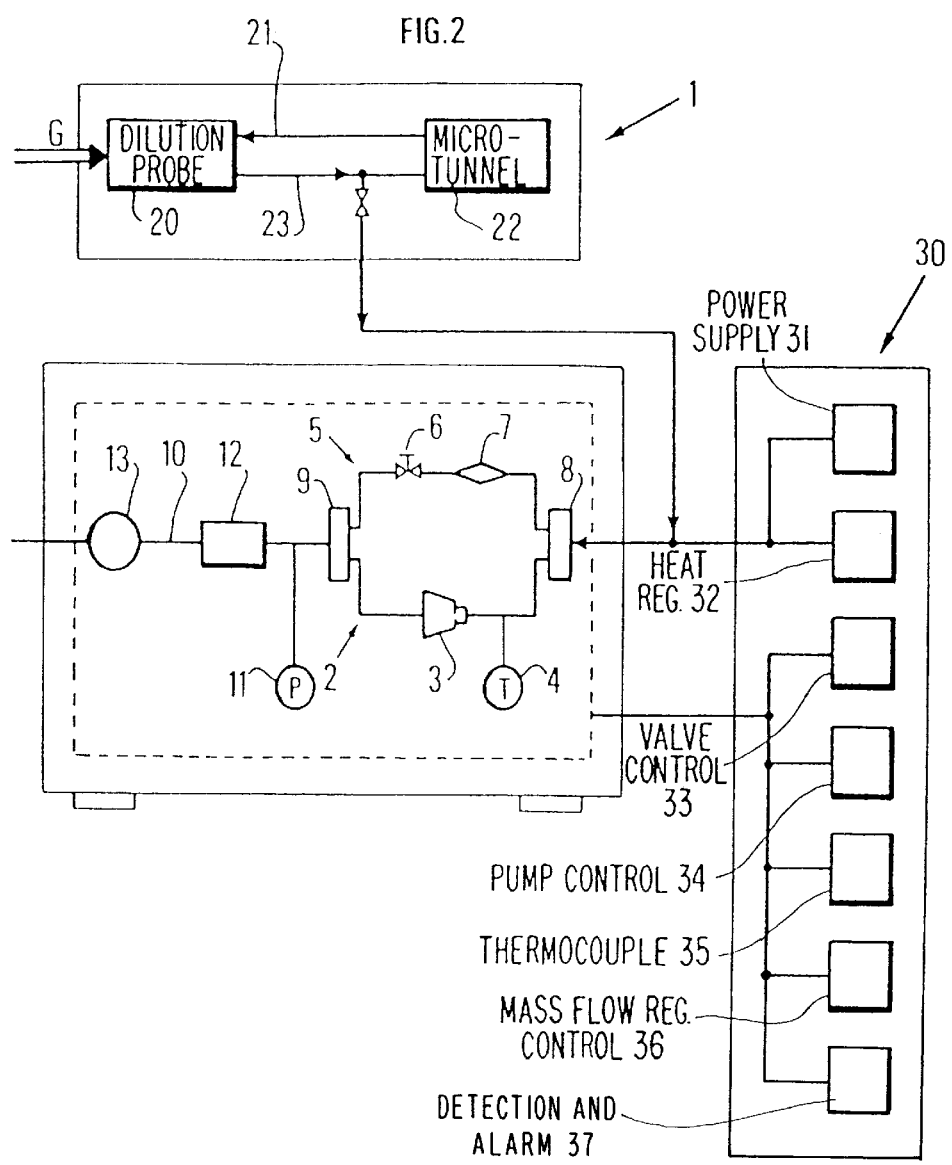

PROCESS AND UNIT FOR SAMPLING ALDEHYDES AND KETONES CONTAINED IN EXHAUST GASES

CROSS REFERENCE TO RELATED APPLICATIONS

This application is a Divisional Application of application Ser. No. 09/344,807, filed Jun. 25, 1999 and now U.S. Pat. No. 6,339,965.

FIELD OF THE INVENTION

The present invention relates to the field of sampling of gaseous fluids and more particularly to the sampling of aldehydes and ketones contained in gases such as exhaust gases of internal-combustion engines. Any gas discharged by thermal combustion engines and containing notably aldehydes and ketones can be sampled according to the invention.

A particular application of the invention relates to the sampling of aldehydes and ketones, non-regulated specific pollutants, discharged in the exhaust gases of automobile engines installed in test cells for example.

BACKGROUND OF THE INVENTION

Known sampling methods mainly consist in diluting the aforementioned gases, then in passing them on a particular solid adsorbent that traps the carbonyl compounds. The chemical trap is treated later in a laboratory where it is analysed in order to quantify individually each pollutant.

Concerning the measurement of aldehydes and ketones in the exhaust oases of cars, most analysis laboratories use either a sampling technique by exhaust gas bubbling in a suitable liquid derivation solution (acetonitrile as the solvent), or a Dinitro-phenylhydrazine-grafted silica cartridge allowing to withdraw and to chemically derive these hydirocarbon-containing species into hydrazone compounds. The grafted cartridge must thereafter be subjected to a treatment in the analysis laboratory that allows these compounds to be brought into solution in a solvent (acetonitrile). The latter sampling and measurement technique has the advantage of being more effective, easy to use and it offers possibilities of medium-term storage of the samples. The hydrazone derivatives obtained by either sampling technique are then separated by injecting an aliquot of this solution into an HPLC (High-Performance Liquid Chromatography) unit and detected individually by UV absorption.

Each laboratory adapts with its own available measuring material and works without interactive connection between the various elements around the sampling support, and without any really reliable, accurate and reproducible sampling protocol.

SUMMARY OF THE INVENTION

The present invention allows the use of commercially available cartridges, fast and sealed setting in a sampling support, simple programming of the sampling parameters, complete sampling automaticity when orders to start trapping of the effluents are given. It provides permanent control of the sampling conditions during the sampling cycle (flow rates, temperatures, pressure drops, sampling time . . . ), immediate alarm in case of malfunction or of failure to respect a procedure.

Furthermore, the present invention eliminates any risk of pollution of the sampling cartridge after it has been installed in its sampling support.

The object of the present invention thus is a unit for sampling aldehydes and ketones contained in previously diluted exhaust oases from thermal combustion engines, comprising an aldehyde and ketone trapping circuit and associated control means.

According to the invention, the unit further comprises:
- a circuit for simulating the passage of the gases into the trapping circuit, arranged parallel to the trapping circuit,
- a means for passing the diluted exhaust gases into either the trapping circuit or the simulation circuit,
- a temperature detector upstream from the trapping means,
- a pressure detector downstream from both circuits,
- a mass flow regulator,
- a means for circulating the gases, such as a pump.

More particularly, the trapping circuit comprises a specific cartridge arranged in series with the temperature detector.

Furthermore, the simulation circuit comprises a filter arranged in series with a throttling means.

The means for selectively diverting the diluted gases towards the trapping circuit or the simulation circuit specifically comprises two three-way solenoid valves situated respectively upstream and downstream from the two parallel circuits.

Furthermore, the unit according to the invention can comprise a means for diluting the exhaust gases.

The dilution means itself can advantageously comprise a dilution probe having an inlet for the gases withdrawn and an outlet connected to the inlet of the sampling circuit, and a microtunnel that cooperates with said probe.

Besides, said microtunnel comprises an outlet connected to the inlet of the dilution probe through a connection for dilution air, the inlet of the microtunnel receiving part of the diluted gases coming from the dilution probe.

Without departing from the scope of the invention, the unit further comprises a detection and alarm means in case of a malfunction of one of its elements.

The present invention further relates to a process for sampling aldehydes and ketones contained in diluted exhaust gases from thermal combustion engines, consisting in trapping said aldehydes and ketones in a specific circuit.

The process according to the invention further consists in passing the diluted gases for some time into a simulation circuit before they are passed into the trapping circuit, the two circuits being arranged in parallel.

According to the invention, the temperature of the gases is controlled in the trapping circuit.

Furthermore, the pressure of the cases is controlled downstream from the simulation circuit and the trapping circuit.

Besides, the gases are passed into the trapping circuit when the composition of the gases is considered sufficiently representative.

BRIEF DESCRIPTION OF THE DRAWINGS

Other features, advantages and details of the invention will be clear from reading the description hereafter, given by way of non limitative example, with reference to the accompanying drawings wherein:

FIG. 1 is a flowsheet of the invention, and

FIG. 2 is a diagram of an embodiment of the invention.

DETAILED DESCRIPTION OF THE INVENTION

The sampling unit as shown in FIG. 1 is associated with dilution means 1 into which the gases flow as shown by double arrow G.

Once diluted, the gases reach the sampling device proper. The latter comprises two parallel circuits (or two channels): the first one is an aldehyde and ketone trapping circuit 2 with, for example, a specific cartridge 3 and a temperature detector 4 situated upstream from cartridge 3. The cartridge can be, for example, a Sep-Pak type DNPH-grafted cartridge marketed by the Waters company.

The second circuit 5 is designed to simulate the pressure drop created by the gas passing on specific cartridge 3. The simulation mainly concerns the flow rate and the pressure drop.

Two three-way solenoid valves 8 and 9 respectively situated upstream and downstream from the two parallel circuits 2 and 5 allow to drive the gaseous flow towards one or other of circuits 2, 5. They thus advantageously allow to isolate cartridge 3 during the simulation phase as explained more in detail hereafter.

A single line 10 allows the gases that have passed through either first circuit 2 or second circuit 5 to flow out of the sampling device.

A pressure detector 11 is situated on outlet line 10 common to both circuits.

A mass flow regulator 12 is also placed on line 10, downstream from detector 11, in order to provide stability of the flow rate in each circuit 2 and 5.

Finally, a circulation pump 13 is arranged downstream from flow regulator 12.

FIG. 2 diagrammatically illustrates a preferred embodiment of the invention.

The same elements as those shown in FIG. 1 appear therein.

Furthermore, FIG. 2 shows more in detail dilution means 1 associated with the sampling unit. The latter can comprise a dilution probe 20 having a first inlet G for the gases to be withdrawn and a second inlet 21 for dilution air coming from a microtunnel 22. Part of the diluted gases flowing from probe 20 enters microtunnel 22. The other part of the gases leaving probe 20 is driven towards the inlet of the sampling device proper.

In the neighborhood of the sampling unit inlet, these gases are kept hot (of the order of about 50° C.) and diluted.

Furthermore, a control unit allows to coordinate the operation of the various elements described above. A control box 30 contains the "electric" part of the sampling unit.

Box 30 allows to program and to display all the parameters connected with the sampling: flow rates, temperatures, durations. Box 30 can be installed in a place remote from the sampling site itself.

This box notably comprises a power supply 31 for the heated line and an element 32 for regulating the heating of said line.

A control 33 for each solenoid valve 8, 9, a control 34 for pump 13, a thermocouple 35 associated with specific cartridge 3, a regulation and display control 36 for mass flow regulator 12 are provided.

Furthermore, detection and alarm means 37 and other malfunction signals may be provided.

A sampling process according to the invention can thus be implemented. It notably consists in passing the diluted gases for some time into simulation circuit 5 before passing them into trapping circuit 2.

The representativeness of the sample at the beginning of the sampling operation proper is thus ensured through a previous circulation of the gaseous effluent in simulation circuit 5.

Besides, through the opening of solenoid valves 8, 9 and through the flow control by means 12, the sampling flow rate is adjusted from the beginning of the trapping operation and throughout the operating cycle.

When the Gaseous effluent is considered representative, i.e. after a given time of passage in circuit 5, solenoid valves 8, 9 lead the gases towards trapping circuit 2.

After a given preprogrammed time of passage in circuit 2, the whole process can be stopped automatically.

After the sampling phase, cartridges 3 are removed from their support and can be treated by an analysis laboratory.

After the sampling phase, the cartridges can advantageously be stored more than 30 days in a freezer (−18° C.) prior to being treated in the analysis laboratory. This functionality is very important in case of a sampling run remote from the analysis site or of a measuring run comprising a large number of samples.

The present invention thus allows to quantify aldehyde and ketone emissions both in an original and simple way. It combines all the necessary functions and elements for ensuring an original, reliable, accurate and reproducible sampling protocol.

It uses commercially available cartridges and thus saves using difficult sampling techniques to implement, such as gas bubbling in a liquid solution. Thanks to its compact design, the present invention can be rapidly installed on the sampling site (transportable). Furthermore, because of its simple parameter programming functions, it can be used by an operator who is not a specialist in analysis.

The present invention has allowed to carry out many measuring runs on themes such as: influence of the nature of the fuel on these carbonyl compounds emissions, influence of the engine running conditions, of new engine technologies or efficiency of devices designed for catalytic treatment of gaseous effluents.

Tests and studies have been carried out to validate the various functions of the device according to the invention, to check its reliability and its trapping efficiency.

In particular, the invention has been implemented to measure aldehyde and ketone emissions discharged by a thermal engine under stabilized running conditions, and according to either the sampling rate or an imposed dilution rate.

What is claimed is:

1. A unit for sampling aldehydes and ketones contained in previously diluted exhaust gases from thermal combustion engines, comprising an aldehyde and ketone trapping circuit (2), associated control means, and further comprising a simulation circuit (5) for simulating passage of the gases in trapping circuit (2), arranged parallel to the trapping circuit, a means (8, 9) for selectively diverting the diluted exhaust gases into either the trapping circuit or simulation circuit (5), a temperature detector (4) upstream from the trapping means, a pressure detector (11) downstream from circuits (2, 5), a mass flow regulator (12), and a means for circulating the gases.

2. A sampling unit as claimed in claim 1, wherein the trapping circuit (2) comprises a sampling cartridge (3) arranged in series with temperature detector (4).

3. A sampling unit as claimed in any one of the previous claims, characterized in that simulation circuit (5) comprises a filter (7) arranged in series with a throttling means (6).

4. A sampling unit as claimed in claim 1, wherein the means for selectively diverting the diluted gases towards trapping circuit (2) or simulation circuit (5) comprise two three-way solenoid valves (8, 9) respectively arranged upstream and downstream from the two parallel circuits (2, 5).

5. A sampling unit as claimed in claim 1, further comprising a means (1) for diluting the exhaust cases.

6. A sampling unit as claimed in claim 5, wherein the dilution means comprises a dilution probe (20) having an inlet (G) for the gases withdrawn and an outlet (23) connected to an inlet of the sampling unit, and a microtunnel (22) that cooperates with said probe.

7. A sampling unit as claimed in claim 6, wherein said microtunnel (22) comprises an outlet connected to the inlet of dilution probe (20) by a connection (21) for dilution air, the inlet of the microtunnel receiving part of the diluted cases from dilution probe (20).

8. A sampling unit as claimed in claim 1, further comprising a detection and alarm means in case of a malfunction of an element of the unit.

9. The sampling unit as claimed in claim 1 wherein the means for circulating the gases is a pump (13).

* * * * *